US010621474B2

(12) United States Patent
Sharma et al.

(10) Patent No.: US 10,621,474 B2
(45) Date of Patent: Apr. 14, 2020

(54) CROWDSOURCING AND DEEP LEARNING BASED SEGMENTING AND KARYOTYPING OF CHROMOSOMES

(71) Applicant: Tata Consultancy Services Limited, Mumbai (IN)

(72) Inventors: Monika Sharma, Gurgaon (IN); Lovekesh Vig, Gurgaon (IN); Shirish Subhash Karande, Pune (IN); Anand Sriraman, Pune (IN); Ramya Sugnana Murthy Hebbalaguppe, Gurgaon (IN)

(73) Assignee: Tata Consultancy Services Limited, Mumbai (IN)

( * ) Notice: Subject to any disclaimer, the term of this patent is extended or adjusted under 35 U.S.C. 154(b) by 145 days.

(21) Appl. No.: 15/895,429

(22) Filed: Feb. 13, 2018

(65) Prior Publication Data

US 2019/0026604 A1 Jan. 24, 2019

(30) Foreign Application Priority Data

Jul. 19, 2017 (IN) .............................. 201721025674

(51) Int. Cl.
*G06K 9/62* (2006.01)
*G16B 10/00* (2019.01)
*G06N 3/04* (2006.01)
*G06N 3/08* (2006.01)
(Continued)

(52) U.S. Cl.
CPC ......... *G06K 9/6262* (2013.01); *G06K 9/0014* (2013.01); *G06K 9/00147* (2013.01);
(Continued)

(58) Field of Classification Search
CPC ................................................ G06K 9/00147
See application file for complete search history.

(56) References Cited

U.S. PATENT DOCUMENTS

2009/0313078 A1* 12/2009 Cross ................. G06K 9/00818
705/7.13
2013/0216118 A1* 8/2013 Rogan .................... G16B 15/00
382/133
(Continued)

FOREIGN PATENT DOCUMENTS

GB 2330907 A * 5/1999 ........... C12Q 1/6827

OTHER PUBLICATIONS

Welinder et al., "Online crowdsourcing: rating annotators and obtaining cost-effective labels", 2010 IEEE Computer Society Conference on Computer Vision and Pattern Recognition Workshops (CVPRW), Jun. 13, 2010, pp. 25-32 (Year: 2010).*
(Continued)

*Primary Examiner* — Nay A Maung
*Assistant Examiner* — Jose Torres
(74) *Attorney, Agent, or Firm* — Finnegan, Henderson, Farabow, Garrett & Dunner LLP

(57) ABSTRACT

The most challenging problems in karyotyping are segmentation and classification of overlapping chromosomes in metaphase spread images. Often chromosomes are bent in different directions with varying degrees of bend. Tediousness and time consuming nature of the effort for ground truth creation makes it difficult to scale the ground truth for training phase. The present disclosure provides an end-to-end solution that reduces the cognitive burden of segmenting and karyotyping chromosomes. Dependency on experts is reduced by employing crowdsourcing while simultaneously addressing the issues associated with crowdsourcing. Identified segments through crowdsourcing are pre-processed to improve classification achieved by employing deep convolutional network (CNN).

8 Claims, 9 Drawing Sheets

(51) Int. Cl.
  G06K 9/00    (2006.01)
  G06T 7/00    (2017.01)
  G16H 30/40   (2018.01)
  G16B 40/20   (2019.01)

(52) U.S. Cl.
  CPC ......... G06K 9/6271 (2013.01); G06N 3/0454 (2013.01); G06N 3/08 (2013.01); G06T 7/0012 (2013.01); G16B 10/00 (2019.02); G06T 2207/20021 (2013.01); G06T 2207/20081 (2013.01); G06T 2207/20084 (2013.01); G06T 2207/30024 (2013.01); G16B 40/20 (2019.02); G16H 30/40 (2018.01)

(56) References Cited

U.S. PATENT DOCUMENTS

2014/0016843 A1* 1/2014 Zhang ............... G06K 9/00147 382/129
2018/0260759 A1* 9/2018 Bencke .......... G06Q 10/063112

OTHER PUBLICATIONS

Irshad et al., "Crowdsourcing Image Annotation for Nucleus Detection and Segmentation in Computational Pathology: Evaluating Experts, Automated Methods, and the Crowd", Pacific Symposium on Biocomputing 2015, pp. 294-305 (Year: 2015).*

Joshi et al., "Efficient karyotyping of metaphase chromosomes using incremental learning", IET Science, Measurement and Technology, 2013, vol. 7, Iss. 5, pp. 287-295 (Year: 2013).*

Poletti et al., "Automatic classification of chromosomes in Q-band images", 30th Annual International IEEE EMBS Conference, Aug. 20-24, 2008, pp. 1911-1914 (Year: 2008).*

Javan-Roshtkhari, M. et al. "A New Approach to Automatic Classification of the Curved Chromosomes," *5th International Symposium on Image and Signal Processing and Analysis*, Sep. 27-29, 2007, Istanbul, Turkey; pp. 19-24.

Sameki, M. et al. "ICORD: Intelligent Collection of Redundant Data—A Dynamic System for Crowdsourcing Cell Segmentations Accurately and Efficiently," *2016 IEEE Conference on Computer Vision and Pattern Recognition Workshops (CVPRW)*, Jun. 26-Jul. 1, 2016, Las Vegas, NV; 10 pages.

Krizhevsky, A. et al. (Jun. 2017). "ImageNet Classification with Deep Convolutional Neural Networks," *Communications of the ACM*, vol. 60, issue 6; pp. 84-90.

Jahani, S. et al. (2012). "Centromere and Length Detection in Artificially Straightened Highly Curved Human Chromosomes," *International Journal of Biological Engineering*, vol. 2, No. 5; pp. 56-61.

* cited by examiner

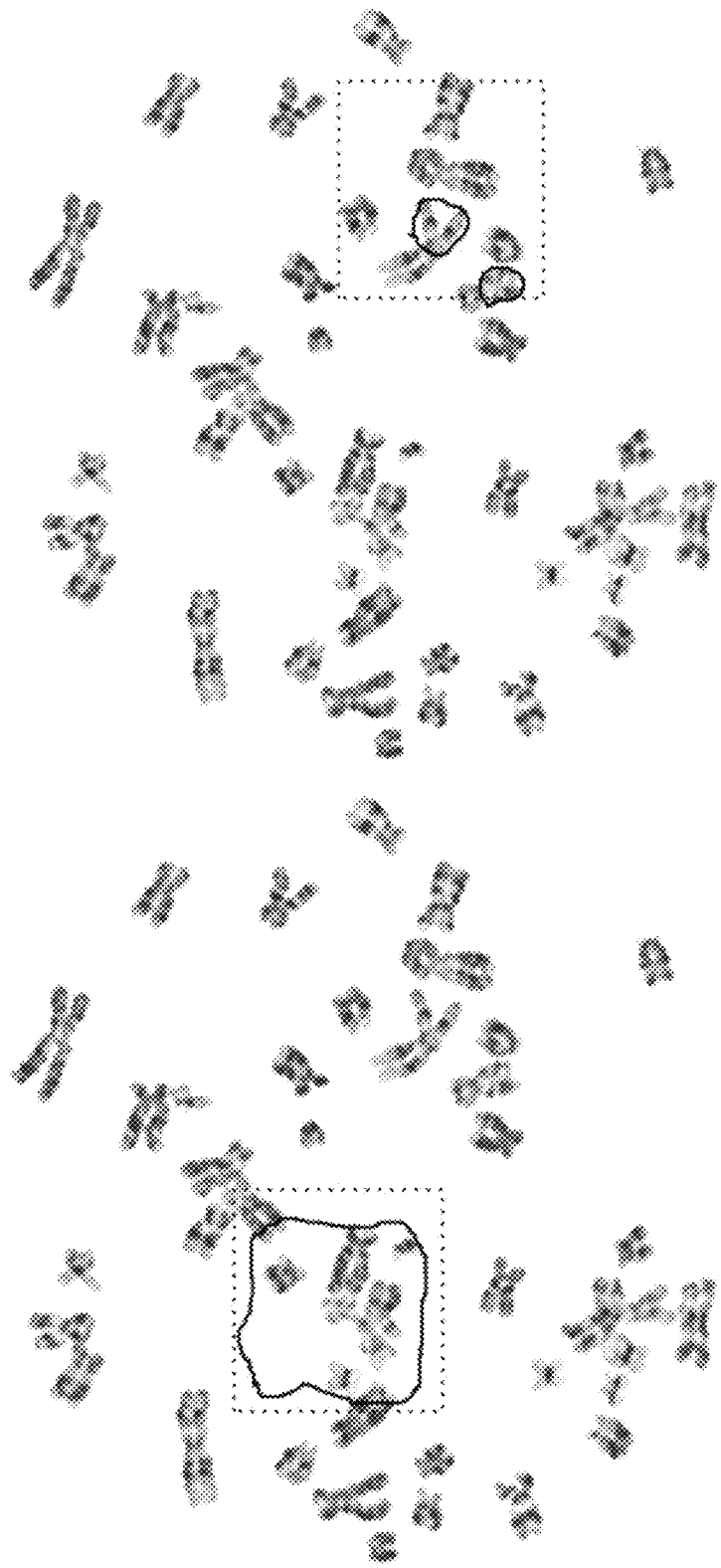

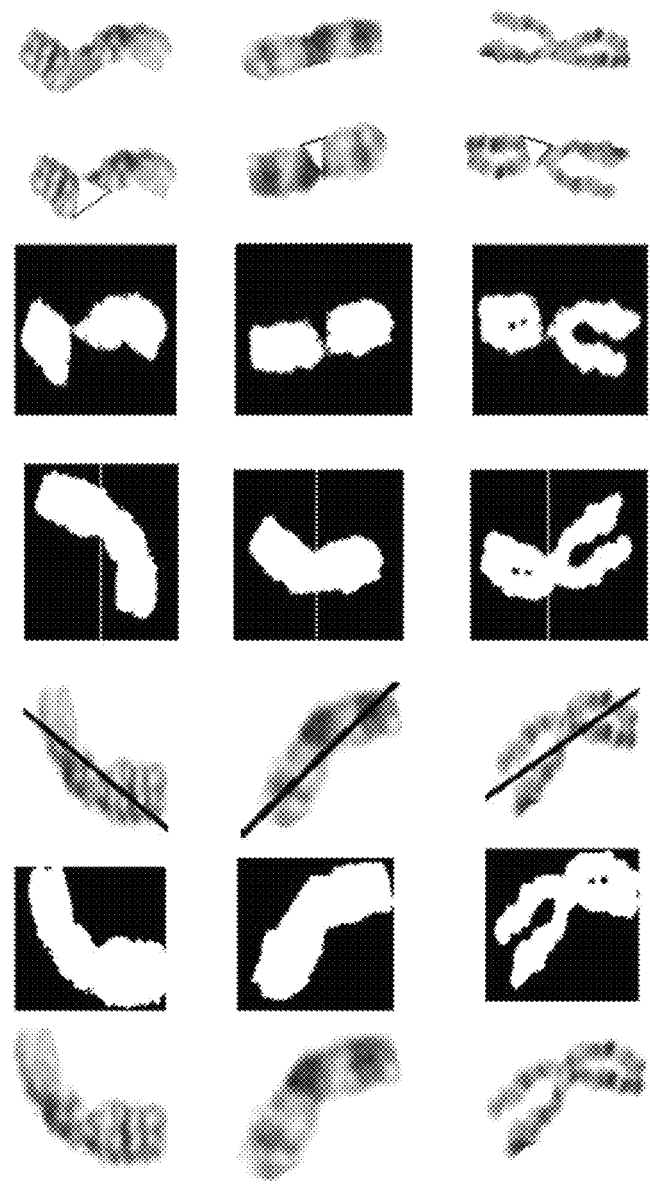

US 10,621,474 B2

CROWDSOURCING AND DEEP LEARNING BASED SEGMENTING AND KARYOTYPING OF CHROMOSOMES

PRIORITY CLAIM

This U.S. patent application claims priority under 35 U.S.C. § 119 to: Indian Patent Application No. 201721025674, filed on 19 Jul. 2017. The entire contents of the aforementioned application are incorporated herein by reference.

TECHNICAL FIELD

The embodiments herein generally relate to cytogenetics, and more particularly to systems and methods for crowdsourcing and deep learning based segmenting and karyotyping of chromosomes.

BACKGROUND

Metaphase chromosome analysis is one of the primary techniques utilized in cytogenetics. Observations of chromosomal segments or translocations during metaphase can indicate structural changes in a cell genome, and is often used for diagnostic purposes. Karyotyping of chromosomes micro-photographed under metaphase is done by characterizing the individual chromosomes in cell spread images. Currently, considerable effort and time is spent to manually segment out chromosomes from cell images, and classify the segmented chromosomes into one of the 24 types, or for diseased cells to one of the known translocated types. Segmenting out the chromosomes in such images can be especially laborious and is often done manually, if there are overlapping chromosomes in the image which are not easily separable by image processing techniques. Many techniques have been proposed to automate the segmentation and classification of chromosomes from spread images with reasonable accuracy, but given the criticality of the domain, a human in the loop is often still required.

SUMMARY

Embodiments of the present disclosure present technological improvements as solutions to one or more of the above-mentioned technical problems recognized by the inventors in conventional systems.

In an aspect, there is provided a processor implemented method comprising receiving digitized images of metaphase chromosomes; optimizing crowdsourcing for segmenting the digitized images, wherein the optimized crowdsourcing comprises: partitioning the digitized images into a plurality of sections; simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section; analyzing the segments received from the one or more workers to identify and eliminate spammers from the crowdsourcing workforce, wherein the analyzing step comprises checking for spurious marking, checking correctness of marking and maximizing coverage of markings; and selecting a set of consensus segments from the analyzed segments for classification based on the analyzes.

In another aspect, there is provided a system comprising: one or more data storage devices operatively coupled to the one or more processors and configured to store instructions configured for execution by the one or more processors to: receive digitized images of metaphase chromosomes; optimize crowdsourcing for segmenting the digitized images, the optimized crowdsourcing comprising: partitioning the digitized images into a plurality of sections; simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section; analyzing the segments received from the one or more workers to identify and eliminate spammers from the crowdsourcing workforce, wherein the analyzing step comprises checking for spurious marking, checking correctness of marking and maximizing coverage of markings; and selecting a set of consensus segments from the analyzed segments for classification based on the analyzes.

In yet another aspect, there is provided a computer program product comprising a non-transitory computer readable medium having a computer readable program embodied therein, wherein the computer readable program, when executed on a computing device, causes the computing device to: receive receiving digitized images of metaphase chromosomes; optimize crowdsourcing for segmenting the digitized images, the optimized crowdsourcing comprising: partitioning the digitized images into a plurality of sections; simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section; analyzing the segments received from the one or more workers to identify and eliminate spammers from the crowdsourcing workforce, wherein the analyzing step comprises checking for spurious marking, checking correctness of marking and maximizing coverage of markings; and selecting a set of consensus segments from the analyzed segments for classification based on the analyzes.

In an embodiment of the present disclosure, the one or more hardware processors are further configured to perform the step of analyzing the segments by one or more filtering steps including: eliminating one or more workers associated with a reliability below a first threshold, wherein the reliability represents number of times a worker's markings is close to a mode of number of segments marked; eliminating one or more workers associated with a quality below a second threshold, wherein the quality represents adversarial markings, markings based on misunderstood instructions and consistently poor segmenting; and eliminating one or more workers associated with number of segments below a third threshold; wherein the first threshold, the second threshold and the third threshold are empirical values.

In an embodiment of the present disclosure, wherein the one or more hardware processors are further configured to classify the set of consensus segments using deep Convolutional Neural Networks (CNN), the step of classifying comprising: straightening bent chromosomes by: binarizing images of the consensus segments, identifying bent chromosomes from the consensus segments using a whiteness value based on a sum of pixel values of the binarized images and total area of a tight fitting rectangle associated with the chromosomes; computing bending orientation of the bent chromosomes based on slope of a fitted line on the binarized images of the consensus segments; computing bending center of the bent chromosomes, wherein the bent chromosomes contain one arm each along a bending axis; and stitching the arms along the bending axis and reconstructing the bent chromosomes to obtain straightened chromosomes. The one or more hardware processors are further configured to normalize lengths of the chromosomes using centromere position and lengths associated thereof; and classify the chromosomes based on the normalized lengths thereof using deep CNN.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which:

FIG. 4A and FIG. 4B illustrate two examples of markings in a pre-defined area of the digitized image of metaphase chromosomes by the crowdsourcing workforce;

FIG. 5A illustrates an original image of a chromosome to be straightened in accordance with an embodiment of the present disclosure;

FIG. 5B illustrates a binarized image of the original image of FIG. 5A;

FIG. 5C illustrates a bending orientation of the chromosome of FIG. 5A;

FIG. 5D illustrates a bending axis of the chromosome of FIG. 5A;

FIG. 5E illustrates stitching of two arms of the chromosome of FIG. 5A;

FIG. 5F illustrates a line drawn as part of reconstruction of the stitched image of FIG. 5E;

FIG. 5G illustrates a final straightened image of the chromosome of FIG. 5A;

Figure 1:
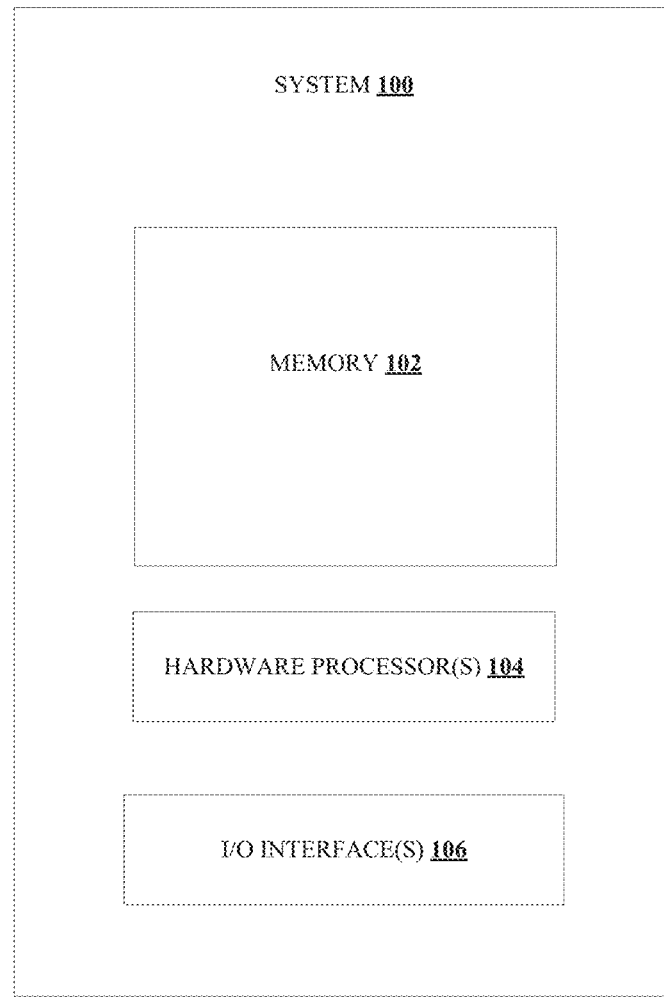
FIG. 1 illustrates an exemplary block diagram of a system for crowdsourcing and deep learning based segmenting and karyotyping of chromosomes, in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Chromosomes are elongated rope like structures in a cell nucleus that contain a human body's genetic code. The human body has 23 pairs of chromosomes. Chromosomal analysis karyotyping is a useful technique to detect genetic abnormalities like Down syndrome, Edwards syndrome, chronic myelogenous leukemia, and Turner syndrome. These abnormalities can manifest in the form of known chromosomal translocations and segments that correspond to different disorders. Karyotyping is performed by culturing cells and during metaphase separating the chromosomes from the nucleus of the cells and staining them on a slide to allow for micro-photography. Finally, the chromosome images are analyzed by experts to classify and segregate the different chromosome segments. Despite the diagnostic importance of karyotyping chromosomes, considerable manual time and effort is required for segmenting out and classifying the chromosomes in images from a cell culture. Systems and methods of the present disclosure aim to reduce the cognitive load involved during segmentation and classification tasks and reduce dependency on experts only to correct errors, if any.

The most challenging problems in karyotyping are segmentation and classification of overlapping chromosomes in metaphase spread images, and numerous attempts have been made in the literature to automate overlapping chromosome segmentation with limited success. This may be because of situations, such as, un-split clusters which could be another main contributor of false positives and chromosome fragmentation that could increase the false negative rate as broken chromosomes cannot be used for further analysis.

One another challenge is that often chromosomes are bent in different directions. There are some vision based methods available for straightening of chromosomes but they are not applicable for chromosomes with varying degrees of bent. Manual effort for ground truth creation via segmentations of microscopic images is an essential step for biomedical analysis. The tediousness and time consuming nature of the task makes it difficult to scale the ground truth for training phase.

Systems and methods of the present disclosure addresses these challenges by providing an end to end solution for machine assisted segmentation and classification of chromosomes that combines use of a non-expert crowd for annotating chromosome segments and a deep classification model for categorizing the individual chromosomes. The systems and methods of the present disclosure relies on a crowdsourcing platform (non-expert crowd) to annotate chromosome boundaries, which are then extracted and fed into a classification engine for karyotyping. Particularly, straightening of bent chromosomes is performed before feeding the chromosome images to a deep neural network for classification to improve the classification accuracy.

Referring now to the drawings, and more particularly to FIGS. 1 through 8, where similar reference characters denote corresponding features consistently throughout the figures, there are shown preferred embodiments and these embodiments are described in the context of the following exemplary system and method.

FIG. 1 illustrates an exemplary block diagram of a system 100 for crowdsourcing and deep learning based segmenting and karyotyping of chromosomes, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2A:
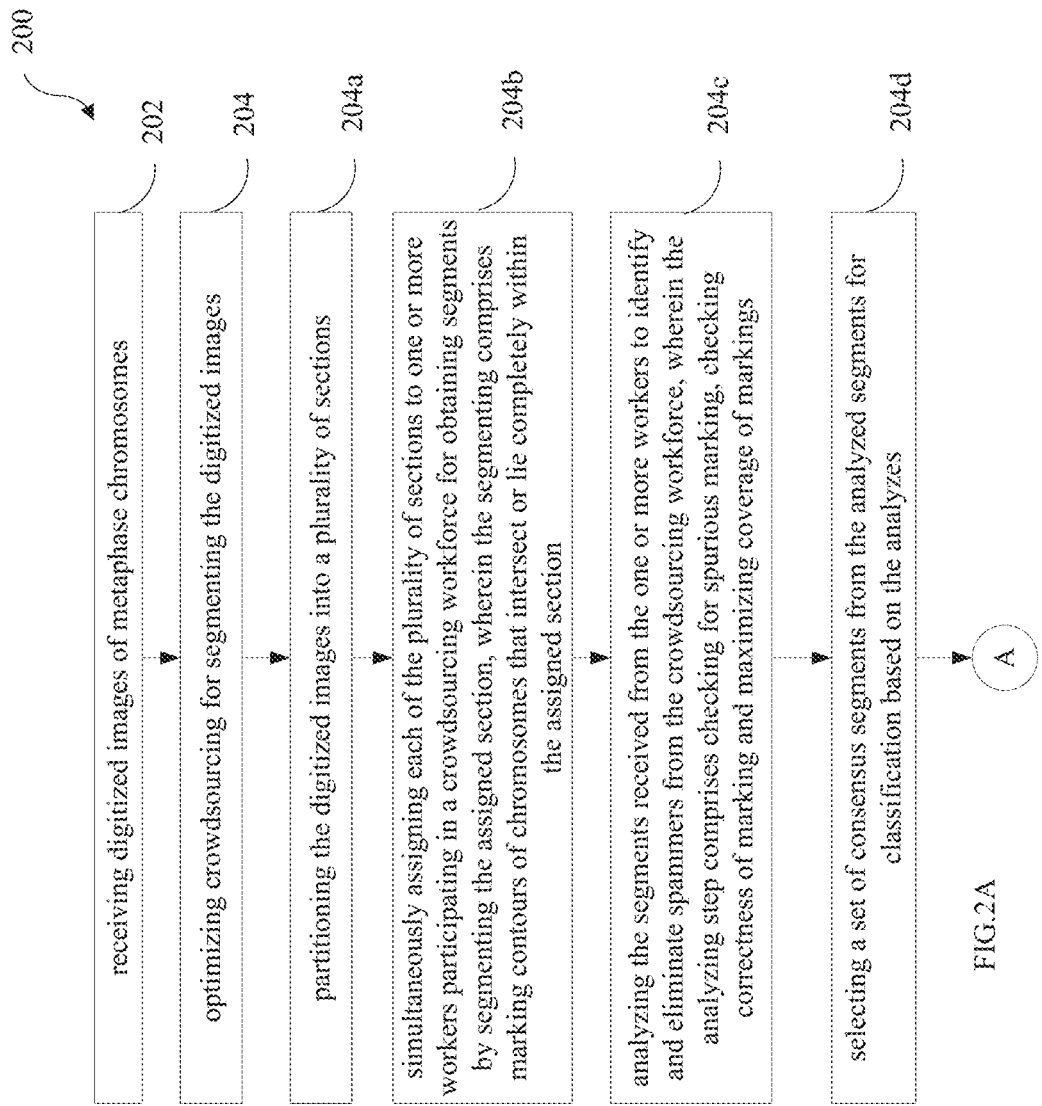
FIG. 2A and FIG. 2B represent an exemplary flow diagram illustrating a computer implemented method for crowdsourcing and deep learning based segmenting and karyotyping of chromosomes, in accordance with an embodiment of the present disclosure.
Figure 2B:
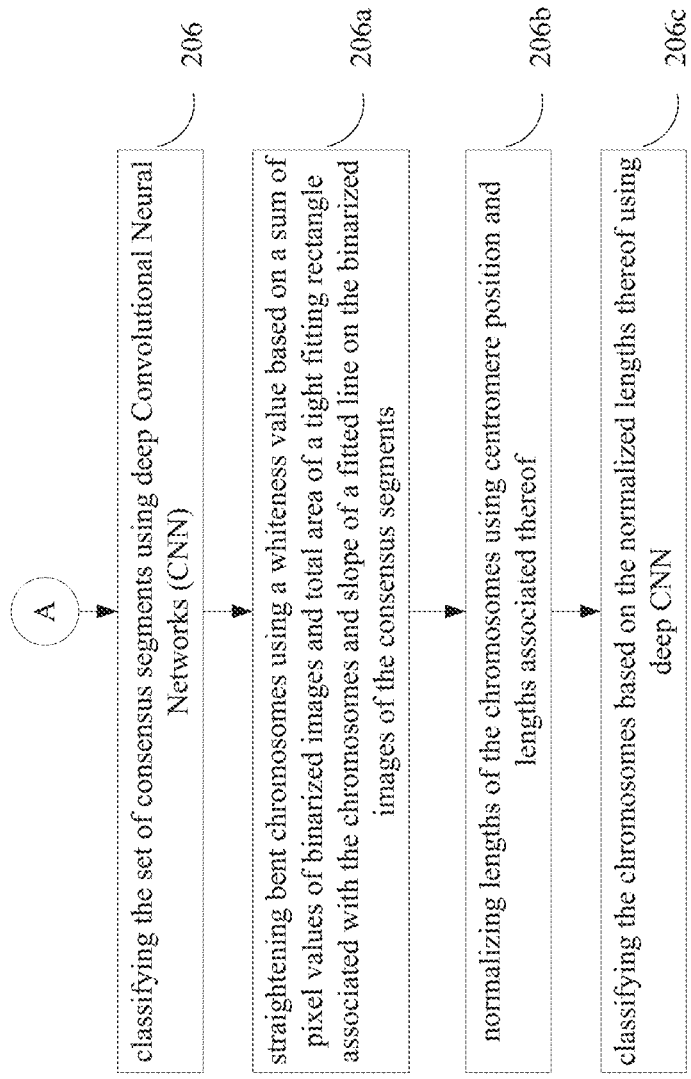

FIG. 2A and FIG. 2B illustrate an exemplary flow diagram illustrating a computer implemented method 200 for crowdsourcing and deep learning based segmenting and karyotyping of chromosomes, in accordance with an embodiment of the present disclosure. In an embodiment, the system 100 comprises one or more data storage devices or memory 102 operatively coupled to the one or more processors 104 and is configured to store instructions configured for execution of steps of the method 200 by the one or more processors 104.

Figure 3B:
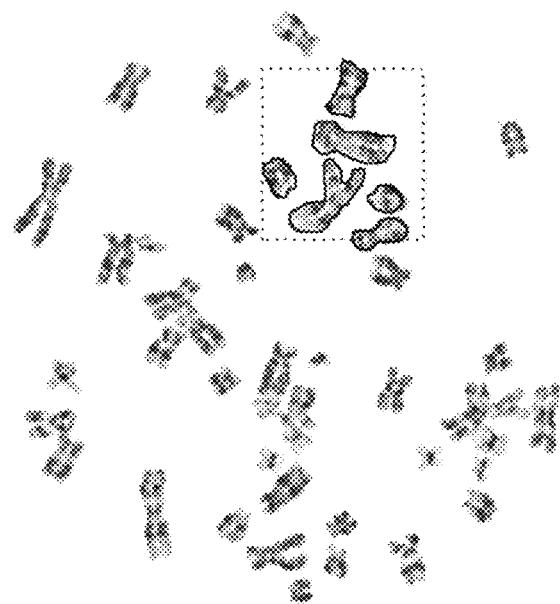
FIG. 3A and FIG. 3B illustrate two examples of markings in a digitized image of metaphase chromosomes by a crowdsourcing workforce.
Figure 3A:
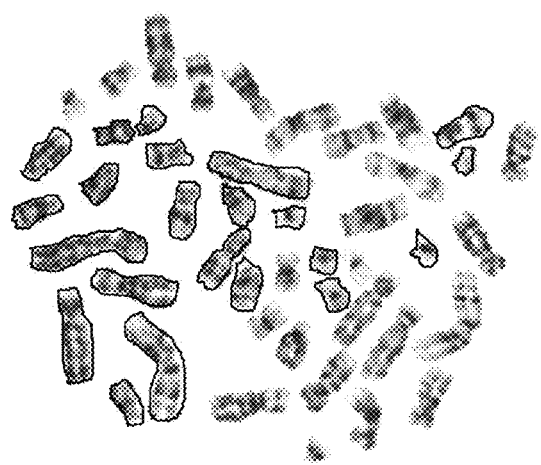

The steps of the method 200 will now be explained in detail with reference to the components of the system 100 of FIG. 1. In accordance with an embodiment of the present disclosure, the one or more processors 104 are configured to receive, at step 202, digitized images of metaphase chromosomes. In accordance with the present disclosure, there is no dependency on experts for segmenting the digitized images. Instead, the methods rely on a non-expert crowd. Workers from CrowdFlower™ were recruited to segment the chromosomes in a given image. Segmenting involves, marking outlines or contours of all chromosomes in an image. FIG. 3A and FIG. 3B illustrate two examples of markings in a digitized image of metaphase chromosomes by the crowdsourcing workforce. Initially, a single worker was required to mark all chromosomes in an image, while creating redundancy by allocating the same image to multiple workers. FIG. 3A particularly illustrates the markings seen in such a scenario. Two drawbacks were noted. Firstly, workers are fatigued and drop off without completing the micro-task. On an average, a worker would only mark≈20 chromosomes. Secondly, as each worker would be cross-evaluated only by another 4 workers who were allocated the same image, there was poor mixing. The key challenges when working with a crowd is to identify spurious or spam markings, as well as maximize coverage. In the context of the present disclosure, markings by spammers (identified as described hereinafter) are referred to as spurious or spam markings. Accordingly, in an embodiment of the present disclosure, the one or more processors 104 are configured to optimize, at step 204, crowdsourcing for segmenting the digitized images. Firstly, in an embodiment, at step 204a, the digitized images are partitioned into a plurality of sections. At step 204b, each of the plurality of sections is simultaneously assigned to one or more workers participating in the crowdsourcing workforce for obtaining segments by segmenting the assigned section. As part of segmenting, the workers were now required to mark chromosomes that intersect or lie completely within an area highlighted by a dotted rectangle as shown in FIG. 3B. By simultaneously assigning a section to multiple workers, redundancy is ensured. Significant coverage improvement was observed. However, several workers would cut a marking off at the border of the dotted line. This effect was addressed with very explicit instructions that provided the workers with screen shots and examples describing chromosome marking across the boundaries. Post these efforts, two types of spammers were observed: workers that were marking a large outline covering all the chromosomes in their grid as illustrated in FIG. 4A and ii) workers not marking/partially marking chromosomes as seen in FIG. 4B. In addition, some of the workers would fuse the marking for overlaid chromosomes, thereby making it necessary to identify and eliminate spammers.

Accordingly, in an embodiment, the one or more processors 104 are configured to analyze, at step 204c, the segments received from the one or more workers. This step helps to identify and eliminate spammers from the crowdsourcing workforce by checking for spurious marking, checking correctness of marking and maximizing coverage of markings. Let there by m workers and n digitized images. Each image may be further partitioned into t sections, with $l_{ij}$ representing the $j^{th}$ part of the $l^{th}$ image. Let $S_{ij}$ be a set of workers who provide segmentation for $l_{ij}$. Let $H_k$ be a set of tuples (i,j) representing the parts that worker k had been assigned. Further, let $c_{ijk}$ be the number of segments marked by the $k^{th}$ worker for $l_{ij}$.

In an embodiment, a filtering step may comprise eliminating one or more workers associated with a reliability below a first threshold, wherein the reliability represents number of times a worker's markings is close to a mode of number of segments marked as explained herein below. Let $C_{ij}$ be the mode of $c_{ijk}$ calculated over set $S_{ij}$. If all workers disagree on the count, then $C_{ij}$ may be declared to be equal to median, and in case of a tie, the higher value may be chosen. Further, in accordance with the present disclosure, a worker's reliability is measured by $$a_k = \sum_{(i,j) \in H_k} 1(|C_{ijk} - C_{i,j}| \le \tau) \quad (1)$$

which represents the number of times a worker is in close agreement with the mode. All workers with reliability below the first threshold may be eliminated. This filtering mechanism removes most obvious spammers who tend to mark segments with little correlation to the true chromosomes.

In an embodiment, another filtering step may comprise eliminating one or more workers associated with a quality below a second threshold, wherein the quality represents adversarial markings, markings based on misunderstood instructions and consistently poor segmenting as described herein below. Let $O_{ijkl}$ be the $l^{th}$ segment marked by worker k on lij. In accordance with the present disclosure, a score $T(O_{ijkl})$ is defined as given below in terms of the best match provided by some other worker:

$$T(O_{ijkl}) = \begin{matrix} \max \\ c \ne k \\ \forall b, c, d \end{matrix} \frac{\text{Area}(O_{ijkl} \cap O_{ibcd})}{\text{Area}(O_{ijkl} \cup O_{ibcd})} \quad (2)$$

Thus, in accordance with the present disclosure, the quality of a worker may be described by the expected quality of his marking, $q(k)=E[t(O_{ijkl})]$. In yet an embodiment, another filtering step may comprise eliminating one or more workers associated with number of segments below a third threshold. Let 1) $[w_1, \ldots, w_N]$ represent n crowd workers,
2) $[a_1, \ldots, a_M]$ represent image sections that have to be marked,
3) Nebw(i) be indices of image sections that worker i has worked upon,
4) Neba(j) be indices of workers who have worked upon region j,
5) $C_{ij}$ be the number of chromosomes marked by worker i for a region j
6) $C_j$ be the true value of the number of chromosomes in image region j
7) $s_i$ be the standard deviation associated with every worker which governs the label noise for the worker, i.e. the label provided by the worker is the true count for region plus zero mean Gaussian random variable with variance $s_i$:

$$C_{ij}=C_j+N(0,s_i)$$

In accordance with the present disclosure, the true value for all $C_j$ and model parameters $s_i$ are to be estimated. In accordance with an embodiment, the hard-Expectation Maximization (EM) may be represented as given below.

Initialization: $c_j = \frac{1}{|Neba(j)|} \sum_{i \in Neba(j)} Cij$

Iterative Steps:

Model Estimation: $s_i = \text{argmax}_{x \in R+} \sum_{j \in Neba(i)} \frac{1}{\sqrt{2\pi x^2}} e^{-\frac{(x-c_j)^2}{2x^2}}$ Label Estimation: $c_j = \text{argmax}_{\mu \in R+} \sum_{i \in Neba(j)} \frac{1}{\sqrt{2\pi s_i^2}} e^{-\frac{(cij-\mu)^2}{2s_i^2}}$ Once the noise quality for all workers is estimated the workers with noise worse than mean $\exp((\log(s_i))+(2*\text{var}(\log(s_i))))$ may be eliminated.

In an embodiment, the first threshold, the second threshold and the third threshold are empirical values.

Once the spammers are identified and eliminated after the analyses at step 204c, a set of consensus segments are selected from the analyzed segments for classification based on the analyses and identification of the best segmentation labels, at step 204d. The consensus chromosomes are selected in a greedy fashion on the basis of the score $T(\cdot)$. Once a segmentation label is selected, labels from all other workers with a significant overlap with the selected marking are removed. This process is repeated till there are no more segmentation labels left to be selected.

In accordance with an embodiment of the present disclosure, the one or more processors 104 are further configured to classify, at step 206, the set of consensus segments using deep Convolutional Neural Networks (CNN). The step of classifying comprises firstly straightening bent chromosomes at step 206a followed by normalizing lengths of the chromosomes at step 206b and finally classifying the chromosomes based on the normalized lengths using deep CNN at step 206c as explained hereinafter.

After the individual chromosomes have been segmented from the digitized images and the consensus segments have been selected at step 204d, they are fed to a classifier to determine the type of chromosome. One of the main challenges in automatic classification of chromosome images obtained from a light microscope is that often chromosomes are bent in different orientations. As the point and extent of bending varies diversely for different chromosomes, the problem of classification becomes more complex. Therefore, in accordance with the present disclosure, an automatic straightening method is employed to straighten the bent chromosomes. The straightening methods known in the art were effective for straightening highly curved chromosomes but may not perform well for slightly less curved chromosomes.

Figure 6B:
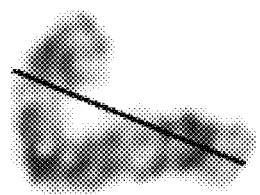
FIG. 6A and FIG. 6B illustrate a chromosome bent towards the left having a negative slope and a chromosome bent towards the right having a positive slope in accordance with an embodiment of the present disclosure.
Figure 6A:
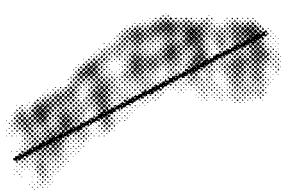

In accordance with the present disclosure, straightening algorithm presented is more widely applicable. This involves some pre-processing steps to improve classification as explained hereinafter. At step 206a, the bent chromosomes are straightened. FIG. 5A through FIG. 5G illustrate steps involved in straightening bent chromosomes, in accordance with an embodiment of the present disclosure. Towards this, firstly original images as seen in FIG. 5A of the consensus segments are binarized as shown in FIG. 5B and bending orientation of the chromosome (FIG. 5C), i.e. whether a particular chromosome is straight or bent is determined. This is done based on the fact that an upright tight fitting rectangle for a straight chromosome contains less blank area as compared to the area for bent chromosomes. Therefore, in accordance with the present disclosure, a whiteness value 'W' is defined as ratio of the sum of pixel values of a binarized chromosome image (which represents the total number of white pixels as all black pixels are of value=0) and total area of the tight fitting rectangle. The chromosomes with $W \geq W_T$ are labeled as straight chromosomes, where $W_T$ is a whiteness threshold whose value is determined empirically to be 170 for the dataset under consideration. Further, the direction of bending of curved chromosomes is determined. A line is fitted to the binarized chromosome as shown in FIG. 5C. and the sign of slope of this line is used to determine the direction of bending of the chromosomes. FIG. 6A and FIG. 6B illustrate a chromosome bent towards the left having a negative slope and a chromosome bent towards the right having a positive slope in accordance with an embodiment of the present disclosure.

In an embodiment, the pre-processing step further comprises computing bending center of the bent chromosomes, wherein the bent chromosomes contain one arm each along a bending axis. Prior to locating a maxima and minima of a horizontal projection vector, the distribution curve of horizontal projection vectors are smoothened out by applying say, a Savitzky Golay filter to ignore small deflections which may contribute to unwanted local maxima or minima. As a result of this step, the chromosomes are split into two sub-images containing one arm each along the bending axis as shown in FIG. 5D, which is where the chromosome is thinnest.

Further, in accordance with an embodiment of the present disclosure, the chromosome arms are stitched along the bending axis and the bent chromosomes are reconstructed to obtain straightened chromosomes. Each sub-image contains one arm of the chromosome which is approximately a straight object. The two sub-images are rotated so that the two arms are in the same direction. For this purpose, each sub-image is rotated from −90° to 90° while its vertical projection vector is calculated at each rotation step. Due to the particular shape of each arm of the chromosome, the vertical projection vector demonstrates minimum width if the arms are in the vertical position inside the sub-image. In a similar manner, the upper arm is rotated so as to be in the vertical position. The stitching of the two arms is done by cropping out the lower black part of aligned upper arm and upper black part for aligned lower arm and shifting upper image horizontally allowing the upper part of the chromosome to lie correctly on the lower part. The shifting is done such that the lowest white pixel of the upper image is just on top of topmost white pixel of lower image as shown in FIG. 5E. As we can see from FIG. 5E, after stitching of the chromosome arms, some pixels of chromosome image are lost. To address this, reconstruction is performed. In this process, the two outer end points (un-joined) of the empty part of the stitched chromosome are found and joined using as single straight line as can be seen in FIG. 5F. The pixels in the area enclosed are then filled with the mean value of the pixels at the same horizontal level as the empty pixel as shown in FIG. 5G. This is done as chromosomes have horizontal bands. Thus, the shade of pixels at the same horizontal level of the straightened chromosome should be the same.

The chromosome segment-images are of varying sizes as a result of segmentation via crowdsourcing. The most distinct features of different chromosomes are the length of chromosomes and the centromere position. To preserve this distinguishing feature, in accordance with the present disclosure, normalizing lengths of the chromosomes is performed, at step 206b, using the centromere position and lengths associated thereof. The chromosome centromere is the thinnest part of the chromosome. For straight chromosomes, the centromere is located by finding out the row number where the sum of row pixels is the lowest, i.e., it has the least number of white pixels or width. In case of curved chromosomes, the bending center is the centromere position.

When a chromosome bends, the surface towards which it is bent contracts in length and the outer surface expands. It is assumed that the length of the medial axis of the object stays the same length after bending. After straightening the chromosome, the true length of the chromosome is calculated by adding together the distance from the center of the upper cut line to the upper edge and the distance from the center of the lower cut line to the lower edge. The true length is normalized across each karyotype image of 23 pairs of chromosomes to a value between 0 and 100.

In humans, each cell normally contains 23 pairs of chromosomes for a total of 46. Twenty-two of these pairs, called autosomes, are identical in both males and females. The 23rd pair, the sex chromosomes X and Y, differ in males and females. In accordance with the present disclosure, at step 206c, the chromosomes are classified based on the normalized lengths obtained at step 206b using deep CNN.

EXPERIMENTAL RESULTS

Dataset: A dataset comprised of 400 stained images with varying degrees of overlap between chromosomes, out of which 200 were kept for testing and the remaining for training and validation.

The efficacy of the methods of the present disclosure was evaluated by considering a control set of 50 images each of which was known to contain 46 chromosomes. However, this fact was not revealed to the crowdsourcing workforce. Each image was divided into (3×3) 9 sections, and each worker was required to provide segmentations for 10 parts chosen from 10 different images.

Figures 7A, 7B, 7C, 7D:
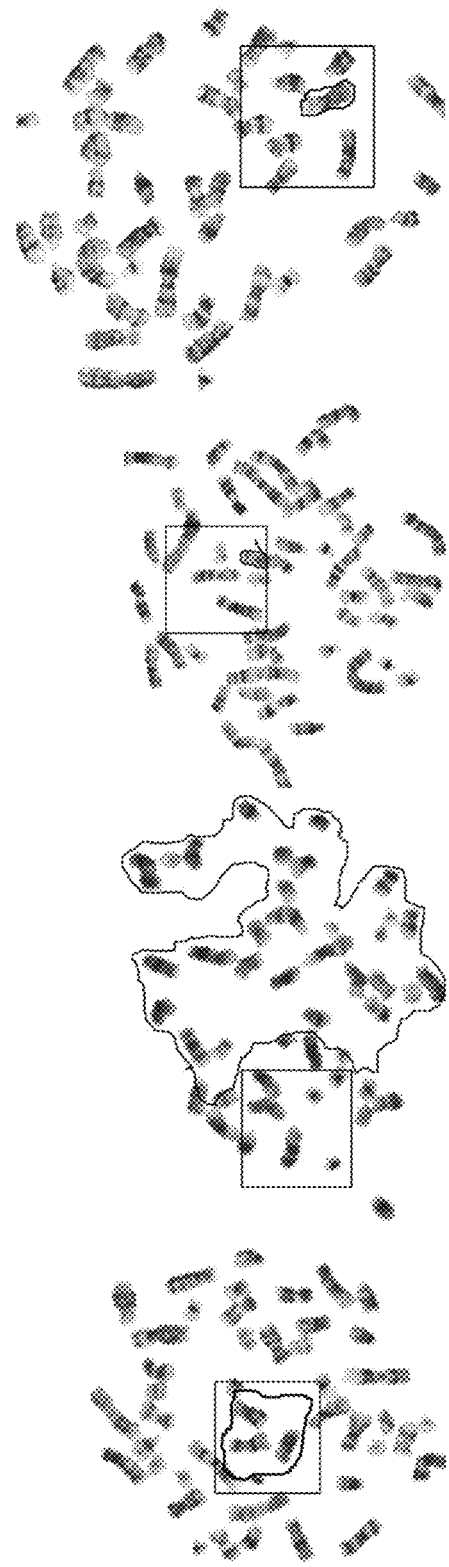
FIG. 7A illustrates an example of responses from the crowdsourcing workforce that were eliminated during filtering in accordance with an embodiment of the present disclosure, wherein one large marking within a grid is identified as a spam.
FIG. 7B illustrates an example of responses from the crowdsourcing workforce that were eliminated during filtering in accordance with an embodiment of the present disclosure, wherein large markings outside a grid are identified as spams.
FIG. 7C illustrates an example of responses from the crowdsourcing workforce that were eliminated during filtering in accordance with an embodiment of the present disclosure, wherein incomplete markings are identified as spams.
FIG. 7D illustrates an example of responses from the crowdsourcing workforce that were eliminated during filtering in accordance with an embodiment of the present disclosure, wherein a marking of only one chromosome per grid is identified as a spam.

A handful of workers left the job without completion and thus a total of 230 workers contributed to the segmenting process. A threshold of $\tau=2$ and $k \geq 3$ was employed as a first step for filtering. This removed the contributions of 32 workers. Further, the mean $T(\cdot)$ score was evaluated for the remaining workers and a threshold of 0.4 was used which removed an additional 91 workers. FIG. 7A through FIG. 7D illustrate examples of responses from the crowdsourcing workforce that were eliminated during filtering in accordance with an embodiment of the present disclosure. The rectangle outlines a section assigned to a worker. The different types of spammers identified were one large marking within the assigned section as illustrated in FIG. 7A, large markings outside the assigned section as illustrated in FIG. 7B, incomplete markings as illustrated in FIG. 7C and markings only one chromosome per grid as illustrated in FIG. 7D. After eliminating the spammers, the step 204d was employed to select a set of consensus segments, however, it was observed that a few spurious markings with very low score of T(·) were not getting eliminated. Hence, a threshold of 0.1 was employed on T(·) to allow for a segmentation label to be selected in the final recommendation.

Figures 8A, 8B, 8C:
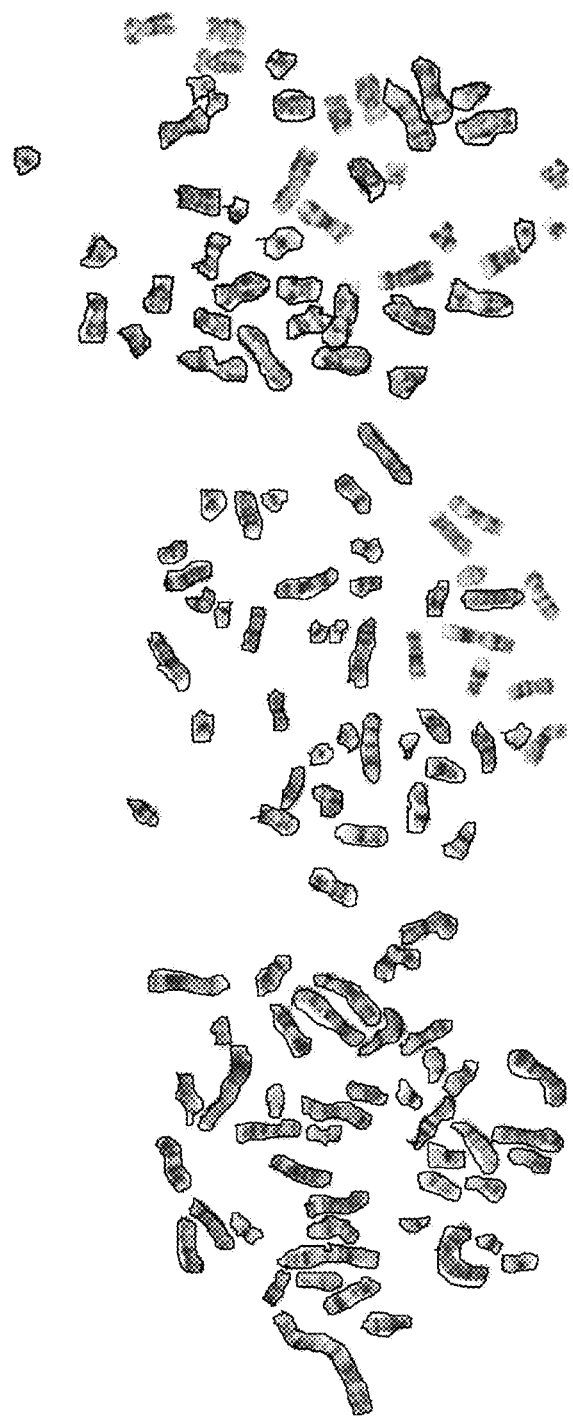
FIG. 8A through FIG. 8C illustrate sample annotations received from the crowdsourcing workforce in accordance with an embodiment of the present disclosure.

After these steps, on an average 35.9 chromosomes per image were identified. FIG. 8A through FIG. 8C illustrate sample annotations received from the crowdsourcing workforce post the filtering and consensus steps in accordance with an embodiment of the present disclosure. 1800 individual chromosome images were manually annotated with their chromosome types, while maintaining class balance. 1600 of these images (derived from the 200 full images in the training set) were used for training and validation sets for training a deep CNN classifier. The trained classifier was tested on the remaining 200 chromosome images (from the 200 full images in the test set). Without straightening and pre-processing, the average classification accuracy obtained was 68.5%. However, with preprocessing, the classification accuracy improved to 86.7%. These results are very likely to improve with more annotated training data for classification.

In accordance with the present disclosure, an interface may be provided to doctors for correcting any errors during crowdsourced segmentation and automated classification. Doctors can select a particular chromosome marking from and focus on its corresponding classification on the interface. If doctors (experts) find any error in either the segmentation or the classification, they can modify these and save the corrected response in the system.

Thus in accordance with the present disclosure, systems and methods described herein above facilitate segmenting and classifying chromosomes using a combination of crowdsourcing, preprocessing and deep learning, wherein a non-expert crowd is utilized to segment out the chromosomes from the cell image (as opposed to clinicians manually segmenting and annotating the chromosome images during karyotyping), which are then straightened and fed into a (hierarchical) deep neural network for classification. Experiments performed using the systems and methods of the present disclosure and results obtained indicate significant reduction in the cognitive burden of segmenting and karyotyping chromosomes. The challenges of spurious or spam markings as well as maximizing coverage of segmentation labels have also been addressed. Furthermore, deep learning has been employed for classification of chromosome images with pre-processing of chromosome segments like straightening of bent chromosomes and chromosome-length normalization before feeding the images to the deep convolutional network (CNN) for classification to improve classification accuracy. The methods and systems of the present disclosure provide a solution in the form of an end-to-end pipeline that yields results which are encouraging and significantly reduce the cognitive burden of segmenting and karyotyping chromosomes. They are computationally less expensive, time-efficient, robust and reliable even in situations where the chromosomes are bent.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (200) comprising:
    receiving digitized images of metaphase chromosomes (202);
    optimizing crowdsourcing for segmenting the digitized images (204), the optimized crowdsourcing comprising:
        partitioning the digitized images into a plurality of sections (204a);
        simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section (204b);
        analyzing the segments received from the one or more workers to identify and eliminate spammers from the crowdsourcing workforce, wherein the analyzing step comprises checking for spurious marking, checking correctness of marking and maximizing coverage of markings (204c) to eliminate the spammers associated with a reliability, quality and a number of segments by comparing with corresponding thresholds; and
        selecting a set of consensus segments from the analyzed segments for classifying the set of consensus segments using deep Convolutional Neural Networks (CNN) to determine a type of chromosome only after straightening bent chromosome.

2. The processor implemented method of claim 1, wherein the step of analyzing the segments comprises one or more filtering steps including:
    eliminating the one or more workers associated with the reliability below a first threshold, wherein the reliability represents number of times a worker's markings is close to a mode of number of segments marked;
    eliminating the one or more workers associated with the quality below a second threshold, wherein the quality represents adversarial markings, markings based on misunderstood instructions and consistently poor segmenting; and
    eliminating the one or more workers associated with the number of segments below a third threshold;
    wherein the first threshold, the second threshold and the third threshold are empirical values.

3. The processor implemented method of claim 1, wherein classifying the set of consensus segments using the deep Convolutional Neural Networks (CNN) (206) comprising:
    binarizing images of the consensus segment;
    identifying bent chromosomes from the consensus segments using a whiteness value based on a sum of pixel values of the binarized images and total area of a tight fitting rectangle associated with the chromosomes;
    computing bending orientation of the bent chromosomes based on slope of a fitted line on the binarized images of the consensus segments;
    computing bending center of the bent chromosomes, wherein the bent chromosomes contain one arm each along a bending axis; and
    stitching the arms along the bending axis and reconstructing the bent chromosomes to obtain straightened chromosomes;
    normalizing lengths of the chromosomes using centromere position and lengths associated thereof (206b); and
    classifying the chromosomes based on the normalized lengths thereof using the deep CNN (206c).

4. A system (100) comprising:
    one or more data storage devices (102) operatively coupled to one or more hardware processors (104) and configured to store instructions configured for execution by the one or more hardware processors to:
        receive digitized images of metaphase chromosomes;
        optimize crowdsourcing for segmenting the digitized images, the optimized crowdsourcing comprising:
            partitioning the digitized images into a plurality of sections;
            simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section;
            analyzing the segments received from the one or more workers to identify and eliminate spammers from the crowdsourcing workforce, wherein the analyzing step comprises checking for spurious marking, checking correctness of marking and maximizing coverage of markings to eliminate the spammers associated with a reliability, quality and a number of segments by comparing with corresponding thresholds; and
            selecting a set of consensus segments from the analyzed segments for classifying the set of consensus segments using deep Convolutional Neural Networks (CNN) to determine a type of chromosome only after straightening bent chromosome.

5. The system of claim 4, wherein the one or more hardware processors are further configured to perform the step of analyzing the segments by one or more filtering steps including:
    eliminating the one or more workers associated with the reliability below a first threshold, wherein the reliability represents number of times a worker's markings is close to a mode of number of segments marked;
    eliminating the one or more workers associated with the quality below a second threshold, wherein the quality represents adversarial markings, markings based on misunderstood instructions and consistently poor segmenting; and
    eliminating the one or more workers associated with the number of segments below a third threshold;
    wherein the first threshold, the second threshold and the third threshold are empirical values.

6. The system of claim 4, wherein the one or more hardware processors classify the set of consensus segments using the deep Convolutional Neural Networks (CNN) comprising:

binarizing images of the consensus segments,
identifying bent chromosomes from the consensus segments using a whiteness value based on a sum of pixel values of the binarized images and total area of a tight fitting rectangle associated with the chromosomes;
computing bending orientation of the bent chromosomes based on slope of a fitted line on the binarized images of the consensus segments;
computing bending center of the bent chromosomes, wherein the bent chromosomes contain one arm each along a bending axis; and
stitching the arms along the bending axis and reconstructing the bent chromosomes to obtain straightened chromosomes;
normalizing lengths of the chromosomes using centromere position and lengths associated thereof; and
classifying the chromosomes based on the normalized lengths thereof using the deep CNN.

7. A computer program product comprising a non-transitory computer readable medium having a computer readable program embodied therein, wherein the computer readable program, when executed on a computing device, causes the computing device to:
receive digitized images of metaphase chromosomes;
optimize crowdsourcing for segmenting the digitized images, the optimized crowdsourcing comprising:
partitioning the digitized images into a plurality of sections;
simultaneously assigning each of the plurality of sections to one or more workers participating in a crowdsourcing workforce for obtaining segments by segmenting the assigned section, wherein the segmenting comprises marking contours of chromosomes that intersect or lie completely within the assigned section;
analyzing the segments received from the one or more workers to identify and eliminate spammers from the crowdsourcing workforce, wherein the analyzing step comprises checking for spurious marking, checking correctness of marking and maximizing coverage of markings to eliminate the spammers associated with a reliability, quality and a number of segments by comparing with corresponding thresholds; and
selecting a set of consensus segments from the analyzed segments for classifying the set of consensus segments using deep Convolutional Neural Networks (CNN) to determine a type of chromosome only after straightening bent chromosome.

8. The computer program product of claim 7, wherein the computer readable program causes the computing device to classify the set of consensus segments using the deep Convolutional Neural Networks (CNN) comprising:
binarizing images of the consensus segments,
identifying bent chromosomes from the consensus segments using a whiteness value based on a sum of pixel values of the binarized images and total area of a tight fitting rectangle associated with the chromosomes;
computing bending orientation of the bent chromosomes based on slope of a fitted line on the binarized images of the consensus segments;
computing bending center of the bent chromosomes, wherein the bent chromosomes contain one arm each along a bending axis; and
stitching the arms along the bending axis and reconstructing the bent chromosomes to obtain straightened chromosomes;
normalizing lengths of the chromosomes using centromere position and lengths associated thereof; and
classifying the chromosomes based on the normalized lengths thereof using the deep CNN.

* * * * *